United States Patent [19]
Breton et al.

[11] Patent Number: 6,153,601
[45] Date of Patent: Nov. 28, 2000

[54] POLYHOLOSIDE COMPOSITIONS FOR STIMULATING THE IMMUNE SYSTEM

[75] Inventors: Lionel Breton, Versailles; Nathalie Pineau, Poitiers; Pierre Desolle, Sevres, all of France

[73] Assignee: Societe l'oreal S.A., Paris, France

[21] Appl. No.: 08/889,793

[22] Filed: Jul. 10, 1997

[30] Foreign Application Priority Data

Jul. 10, 1996 [FR] France .................................. 96-08617

[51] Int. Cl.$^7$ .......................... A61K 31/715; C07H 1/00
[52] U.S. Cl. ....................... 514/54; 536/123.1; 424/401
[58] Field of Search .......................... 514/54; 536/123.1; 424/401

[56] References Cited

U.S. PATENT DOCUMENTS

| | | | |
|---|---|---|---|
| 4,298,691 | 11/1981 | Veeder et al. | 435/101 |
| 4,512,983 | 4/1985 | Shino et al. | 424/195.1 |
| 5,374,655 | 12/1994 | Kashem et al. | 514/540 |
| 5,622,718 | 4/1997 | Al-Shamkhani et al. | 424/488 |
| 5,876,982 | 3/1999 | Paul et al. | 435/101 |

FOREIGN PATENT DOCUMENTS

| | | |
|---|---|---|
| 4221753 | 7/1994 | Germany . |
| 96/23057 | 8/1996 | WIPO . |

OTHER PUBLICATIONS

Drug Research, vol. 35, No. 7, 1985, pp. 1069–1075, XP000646167, Wagner et al, abstract only translated, month not available.

*Primary Examiner*—Kathleen K. Fonda
*Attorney, Agent, or Firm*—Burns, Doane, Swecker & Mathis, L.L.P.

[57] ABSTRACT

Cosmetic/pharmaceutical/dermatological compositions suited for stimulating the immune system/defenses of a mammalian organism, via topically applying same to the skin of such organism, comprise an immune system-stimulating amount of at least one polyholoside which comprises at least one fucose structural unit, preferably a heterogeneous polyholoside, in a topically applicable, cosmetically/pharmaceutically/dermatologically acceptable vehicle, carrier or diluent therefor.

10 Claims, No Drawings

POLYHOLOSIDE COMPOSITIONS FOR STIMULATING THE IMMUNE SYSTEM

CROSS-REFERENCE TO COMPANION APPLICATION

Copending application Ser. No. 08/891,194, filed Jul. 10, 1997 and assigned to the assignee hereof.

BACKGROUND OF THE INVENTION

1. Technical Field of the Invention

The present invention relates to the formulation of effective amounts of at least one polyholoside into cosmetic/pharmaceutical/dermatological compositions, in particular for topical application, for stimulating the immune system/defenses.

2. Description of the Prior Art

The immune system comprises a spectrum of specialized cells subjected to multiple mechanisms of control ensuring their renewal, their activation and their differentiation, which are essential to a normal level of immunocompetence. The role of the immune system is to discriminate the self from the non-self in order to eliminate pathogenic agents and spontaneous tumors. Any cell depletion, any immune dysregulation or any functional deficiency is likely to promote the onset of pathological manifestations characterized by the disruption of the mechanisms for recognition of the self from the non-self, and a greater sensitivity towards microbial aggressions or challenges and neoplastic processes.

The skin is arguably the most important organ of the body and is recognized as one of the principal active components of the immune defense system. Three types of epidermal cells participate in this system: the keratinocytes, melanocytes and the Langerhan's cells. These cells, which exist only at the level of the skin, play a key role in the immune response and, in particular, in antigenic presentation.

Healthy skin, by its very nature, is capable of defending itself from external adverse aggressions and challenges. However, it is subjected to constant aggression/challenge from the environment, chemical products, and radiation. In particular, the Langerhan's cells are the preferred target of ultraviolet radiation.

These adverse influences result in an immune defense suppressing effect causing a reduction in resistance to pathogenic agents and an increase in the incidence of certain cancers.

To assist the skin in fulfilling its immune function, products for cutaneous immune system stimulation are of great interest.

It is known, moreover, that the immune system and, more particularly, that of the skin, weakens or deteriorates during chronobiological aging.

This weakening also occurs during photoinduced aging. An immunostimulating effect can then reestablish the immune functions and, more particularly, those of the epidermis, by reinforcing the natural defenses of the skin.

SUMMARY OF THE INVENTION

Accordingly, a major object of the present invention is the provision of novel immunostimulants, more particularly for stimulating the immune system of mammalian skin.

Briefly, it has now unexpectedly been determined that topically applying effective amounts of at least one polyholoside to the skin, each such polyholoside comprising at least one fucose structural unit, stimulates the immune defenses thereof.

DETAILED DESCRIPTION OF BEST MODE AND SPECIFIC/PREFERRED EMBODIMENTS OF THE INVENTION

More particularly according to the present invention, it is known that the saccharides of formula $C_n(H_2O)_n$ are generally divided into two categories: the monosaccharides or simple sugars, and the saccharides or the association of several molecules.

Among the saccharides, there may be distinguished (1) the holosides which are formed solely of sugars and (2) the heterosides which comprise one or more monosaccharides and a non-carbohydrate moiety.

Further, among the polyholosides, there may also be distinguished the homogeneous polyholosides which result from the association of the same monosaccharide, and the heterogeneous polyholosides which result either from the association of different monosaccharides, or from the association of monosaccharides having the same empirical chemical formula but of different geometric or optical configuration (D and L isomers for example), also considered herein as different monosaccharides.

It is this latter category, i.e., the heterogeneous polyholosides, which is the more preferred according to the present invention.

The heterogeneous polyholosides according to the invention comprise only sugars and result from the association of at least two different monosaccharides, of which at least one is a fucose.

The polyholosides of this invention advantageously comprise 2 to 10 monosaccharides, compounds commonly designated oligoholosides, or more than 10 monosaccharides, compounds commonly designated polyholosides.

The monosaccharides comprising the polyholosides according to the invention may be selected from among all possible monosaccharides, of natural or synthetic origin, and especially:

(a) the aldoses such as:
  (i) the pentoses, for example ribose, arabinose, xylose or apiose;
  (ii) the hexoses, for example glucose, fucose, mannose or galactose;
(b) the ketoses, such as fructose;
(c) the deoxyoses, such as rhamnose, digitoxose, cymarose or oleandrose,
(d) the monosaccharide derivatives, such as uronic acids, for example mannuronic, guluronic, galacturonic or glycuronic acids, or the itols such as mannitol or sorbitol.

According to this invention, preferred are heterogeneous polyholosides which comprise at least two monosaccharides of which at least one is a fucose and the other is selected from among ribose, arabinose, xylose, apiose, glucose, mannose, galactose, fructose, digitoxose, cymarose, oleandrose, uronic acids and itols.

The present invention therefore features, as the active agent in a cosmetic composition, or for the formulation of a pharmaceutical, in particular a dermatological, composition, an effective amount of at least one polyholoside comprising at least one fucose structural unit, such polyholoside or composition comprised thereof being well suited for stimulating the immune defenses.

The polyholosides according to the invention present, in addition, other advantages. This makes it possible to formulate a composition for the skin which is not very irritant or non-irritant and not very sticky, which exhibits, moreover, a soft and pleasant feel. Another advantage presented by such a polyholoside is to enhance the stabilization of the final composition, when it is provided in the form of an emulsion, by virtue of the self-emulsifying properties of the particular polyholoside, in particular when it is a polyholoside comprising a fucose unit.

Too, the formulation of a polyholoside into compositions, especially cosmetic compositions, permits the production of a gelled composition without further addition of a conventionally employed gelling agent. The gel obtained is smooth and unctuous.

Still more preferably, the polyholoside comprises fucose, galactose and galacturonic acid structural units, and more particularly a linear linkage or complexing of $\alpha$-L-fucose, $\alpha$-D-galactose and galacturonic acid.

Preferably, the heterogeneous polyholoside comprises at least one fucose unit, which is advantageously present in an amount of 10%–90% by weight, preferably 15%–35% by weight, relative to the weight of the polyholoside dry solids.

Per the present invention, a heterogeneous polyholoside alone, or a mixture of heterogeneous polyholosides, may be used.

The polyholoside according to the invention may be an alginate (polymannuronate and -guluronate), such as a sodium alginate, a propyleneglycol alginate, a calcium alginate, or a glyceryl alginate.

The polyholoside according to the invention may be optionally branched or linear. It may also be substituted, for example by fatty chains, especially comprising 8 to 30 carbon atoms.

The polyholoside of this invention may be of any origin, natural or synthetic. In particular, a polyholoside prepared from a microorganism, such as for example *Klebsiella pneumoniae* is employed. Still more particularly, a polyholoside prepared from the strain *Klebsiella pneumoniae* subsp. *Pneumoniae*, termed BEC 1000, is employed.

When a polyholoside of natural origin, produced from a microorganism, is used, it is generally associated with proteins. It may then be subjected to a proteolytic treatment.

Any technique permitting the hydrolysis of the proteins may then be used, preferably an enzymatic hydrolysis.

The polyholoside is advantageously present in the final composition in an amount of $10^{-4}\%$ to 20% by weight relative to the weight of the composition, and preferably of $10^{-3}\%$ to 10% by weight relative to the weight of the composition.

The polyholoside preferably has a viscosity of 800–1,200 mPa.s (Brookfield LV31 viscosity, 12 revolutions/min, at 30° C.) when it is dissolved in water, at a concentration of about 1% by weight.

Thus, the present invention also features medicaments comprising a polyholoside as described above, other than an alginate.

In another embodiment of the invention, cosmetic/pharmaceutical compositions comprise, as the active ingredient therefor, at least one polyholoside as described above, other than an alginate.

The subject pharmaceutical compositions preferably are for dermatological uses.

The subject pharmaceutical compositions are particularly well suited for stimulating the immune defenses, and still more particularly for stimulating the immune defenses of the skin.

The polyholoside is advantageously present in the compositions according to the invention in an amount of $10^{-4}\%$ to 20% by weight relative to the total weight of the composition and preferably from $10^{-3}\%$ to 10% by weight relative thereto.

The polyholosides of this invention may therefore be formulated as an agent for stimulating the immune defenses, in particular into a composition for hair use or into a composition for the skin of the body and/or of the face.

The subject compositions include a topically applicable, cosmetically/pharmaceutically/dermatologically acceptable vehicle, diluent or carrier therefor and may be provided in the form of an emulsion, especially an oil-in-water or a water-in-oil emulsion, or in the form of a multiple emulsion. It may also be provided in the form of an aqueous solution, optionally gelled, in the form of a lotion, for example a two-phase lotion, of a cream, a milk, an ointment, or a foam.

The subject compositions may comprise an oily phase based on animal, vegetable, mineral, silicone, fluorinated and/or synthetic oil.

The oily phase may also comprise fatty alcohols or fatty acids, as well as surfactants.

Particularly exemplary thereof are the hydrocarbon oils, such as paraffin oil or petroleum jelly; perhydrosqualene; arara oil, sweet almond, calophyllum, palm, castor, avocado, jojoba, olive or cereal germ oil; alcohols such as oleyl alcohol, linoleyl or linolenoyl alcohol, isostearyl alcohol or octyl dodecanol. Also exemplary are the silicone oils, such as PDMS, optionally phenylated, such as phenyltrimethicones.

The oily phase may also comprise a makeup removing oil such as a fatty acid ester, in particular the esters derived from a straight or branched chain alcohol having from 1 to 17 carbon atoms and from a straight or branched chain fatty acid having from 3 to 18 carbon atoms.

Particularly representative such esters include dioctyl adipate, 2-ethylhexyl palmitate, diisopropyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethyl hexanoate, 2-ethylhexyl octanoate, 2-ethylhexyl caprate/caprylate, methyl palmitate, butyl myristate, isobutyl myristate, ethyl palmitate, isohexyl laurate, hexyl laurate, isopropyl isostearate.

The oily phase is advantageously present in an amount of from 5%–95% by weight in the case of an emulsion.

The compositions of this invention may also comprise:

(a) an agent permitting the suspension of the fatty phase, for example a copolymer of $C_{10}$–$C_{30}$ alkyl acrylates and of acrylic or methacrylic acid, or of ester thereof (Pemulen TR1, Pemulen TR2, Carbopol 1342 from GOODRICH); or an acrylamide/methylpropanesulfonic acid copolymer (Sepigel marketed by SEPPIC), and/or (b) an agent for dispersing the fatty phase, such as an emulsifying system or a vesicular system based on vesicles, optionally of nanometric size, comprising ionic lipids (liposomes) or nonionic lipids, and in particular the emulsifying systems well known to this art, comprising glyceryl stearate/PEG 100 stearate (CTFA), cetyl alcohol and stearyl alcohol.

The compositions of the invention too may comprise, in addition, an agent for modifying their viscosity, and for providing textures which are gelled to a greater to lesser degree, such as:

(i) the cellulosic derivatives (carboxymethylcellulose, hydroxyethylcellulose, hydroxypropylmethylcellulose);

(ii) the natural gums, such as xanthan, guar, carob gums, scleroglucans, chitin or chitosan derivatives, carrageenans;

(iii) the polycarboxyvinyl derivatives of the Carbomer type (marketed by GOODRICH under the trademarks Carbopol, 940, 951, 980 or by 3V-SIGMA under the trademarks Synthalen K or Synthalen L).

The compositions according to the invention may also comprise, in known fashion, adjuvants and additives commonly used in this art, such as preservatives, antioxidants, perfumes, fillers such as kaolin or starch, or even hollow microspheres, pigments, colorants, UV-screening agents, sequestrants, essential oils, hydrophilic or lipophilic active agents such as moisturizers, especially glycerin, butyleneglycol, anti-inflammatory agents such as allantoin, bisabolol, anti-free radical agents such as vitamin E or derivatives thereof, soothing agents such as bluet or cornflower water, plant extracts, depigmenting agents, biological active agents such as urea, amino acids, vitamins and derivatives thereof, proteins, salicylic acid and derivatives thereof, α-hydroxy acids, pyrrolidonecarboxylic acid and its salts, ceramides.

Of course, one skilled in this art will take care to select this or these optional additional compounds, and/or the amounts thereof, such that the advantageous properties of the compositions according to the invention are not, or are not substantially, adversely affected by the additions envisaged.

The subject compositions preferably have a pH which does not adversely affect the skin, generally ranging from 5 to 8, preferably a pH of 5.5 to 7.5.

In order to further illustrate the present invention and the advantages thereof, the following specific examples are given, it being understood that same are intended only as illustrative and in nowise limitative.

EXAMPLE 1

The capacity of a fucose-rich polyholoside (O.F.) to stimulate the immune defenses was studied in this example.

The test was carried out on a polyholoside prepared from the strain *Klebsiella pneumoniae* subsp. *Pneumoniae*, which had been subjected to a proteolytic treatment (O.F.).

This polyholoside, having a molecular weight of less than 10,000 Da, was obtained in the laboratory after hydrolysis of a bacterial polysaccharide fraction. This molecule exhibited, in particular, the following activities (activities representative of immunostimulant activity):

1. Study of the stimulation of mouse splenocytes:

| Concentration in mg/ml | 0.5 | 1 | 5 | 10 |
|---|---|---|---|---|
| O.F. | 299 | 722 | 868 | 466 |

The results are expressed as percentage stimulation relative to the control whose value was equal to 100. Any value above 200 was considered to be positive.

An increase in the proliferation of the mouse splenocytes corresponded to a stimulant effect of the product on the T and/or B cells.

The fucose-rich oligosaccharide activated the proliferation of the mouse splenocytes; it was, therefore, a potential immunostimulant.

2. Study of the production of immunoglobulins by mouse splenocytes:

|  | IgG1 | IgG2a | IgG2b | IgG3 | IgM | IgA |
|---|---|---|---|---|---|---|
| 1 mg/ml | 209.6 | 126.5 | 107.9 | 111.1 | 105.4 | 101.2 |
| 5 mg/ml | 235.8 | 198.2 | 184.7 | 172.9 | 122.7 | 146 |
| 10 mg/ml | 285 | 134.1 | 205.2 | 204.9 | 124 | 145.8 |

The results are expressed as percentage stimulation relative to the control whose value was equal to 100.

As indicated above, a positive effect on the production of immunoglobulins represented immunostimulation and provided additional information to be taken into account, since it likely indicated a specific effect of the B cells. The B cells have a very important role in the immune response which results in:

(a) a production of antibodies, (b) an antigen presenting function.

The fucose-rich oligosaccharide, therefore, had a specific activity on the B cells.

In conclusion, all the results presented above indeed confirmed the immunostimulant role of this oligosaccharide prepared from a polysaccharide fraction of bacterial origin.

EXAMPLE 2

Examples of formulations illustrating the invention. These compositions were formulated simply by intimately admixing the various components.

| O.F.* | 10 g |
|---|---|
| Glyceryl monostearate, polyethyleneglycol stearate (100 EO) | 3 g |
| Carboxyvinyl polymer | 0.4 g |
| Stearyl alcohol | 0.7 g |
| Soya bean proteins | 3 g |
| NaOH | 0.4 g |
| Preservative | qs |
| Water     qs | 100 g |

This composition was provided in the form of a milk for the face, having good cosmetic properties, and being soft and comfortable to use.

The pH of the composition was about 5.5.

Composition 2 (Lotion):

| O.F.* | 5.00 g |
|---|---|
| 2-ethylhexyl palmitate | 10.00 g |
| Cyclopentadimethylsiloxane | 20.00 g |
| Butyleneglycol | 5.00 g |
| Preservative | qs |
| Water     qs | 100 g |

This lotion, which did not contain a surfactant, promoted desquamation of the skin.

Composition 3 (Milk):

| Octyl palmitate | 35.00 g |
|---|---|
| Glycerin | 2.00 g |
| O.F.* | 0.50 g |
| Crosslinked polymer $C_{10}$–$C_{30}$ acrylates/alkyl acrylates | 0.10 g |
| Triethanolamine | 0.10 g |

-continued

|  |  |
|---|---|
| Wheat amino acids | 1.00 g |
| Preservative | qs |
| Water    qs | 100 g |

The milk obtained, which did not contain a surfactant, had good cosmetic properties.

Composition 4 (Gel for the face):

|  |  |
|---|---|
| Glycerin | 10.00 g |
| O.F.* | 2.00 g |
| Sodium cocoamphodiacetate | 1.00 g |
| Preservative | qs |
| Water    qs | 100 g |

The gel obtained had good cosmetic properties.

Composition 5 (Water-based cleansing gel):

|  |  |
|---|---|
| Butylene glycol | 7.00 g |
| Sodium lauroyl sarcosinate | 4.00 g |
| O.F.* | 0.04 g |
| Triethanolamine | 0.80 g |
| Carbomer | 0.50 g |
| Preservative | qs |
| Water    qs | 100 g |

O.F.*: polyholoside comprising fucose, galactose and galacturonic acid prepared from the strain *Klebsiella pneumoniae* subsp. Pneumoniae, which had been subjected to a proteolytic treatment, marketed by Solabia.

The gel obtained had good cosmetic properties.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

The strain of *Klebsiella pneumoniae* subspecies Pneumoniae (BEC 1000) utilized in the Example to produce the exemplified polyholoside was deposited in the Collection Nationale de Cultures de Microorganismes, 25, rue du Docteur Roux, 75724 Paris Cedex 15, France on Dec. 16, 1994 in accordance with the provisions of the Budapest Treaty. This microorganism was accorded Accession No. I-1 507. This strain was disclosed and claimed in U.S. Pat. No. 5,876,982, issued on Mar. 2, 1999.

What is claimed is:

1. A cosmetic/pharmaceutical/dermatological method for stimulating the immune response comprising topically applying an immunostimulating effective amount of a polyholoside which comprises fucose, galactose, and galacturonic acid structural units, and a cosmetically/pharmaceutically/dermatologically acceptable carrier therefor.

2. The method of claim 1, wherein said polyholoside comprises α-L-fucose, α-D-galactose and galacturonic acid.

3. The method of claim 1, wherein the amount of fucose in said polyholoside constitutes 10 to 90% by weight thereof.

4. The method of claim 1, wherein said polyholoside is isolated from a microorganism.

5. The method of claim 4, wherein said microorganism is a strain of *Klebsiella pneumoniae*.

6. The method of claim 5, wherein said strain is *Klebsiella pneumoniae*, sub-species Pneumoniae (BEC 1000), which has been accorded Accession No. 1-507.

7. The method of claim 1, which comprises a form selected from the group consisting of an emulsion, an aqueous solution which is optionally gelled, a lotion, a two-phase lotion, cream, milk, and a foam.

8. The method of claim 1, wherein the amount of said polyholoside comprises from $10^{-3}\%$ to 10% by weight thereof.

9. The method of claim 1, which has a pH ranging from 5 to 8.

10. The method of claim 1, further comprising at least one additional ingredient selected from the group consisting of at least one preservative, antioxidant, perfume, filler, kaolin, starch, hollow microspheres, pigment, colorant, UV-screening agent, sequestrant, essential oil, hydrophilic or lipophilic active agent, moisturizer, glycerin, butyleneglycol, anti-inflammatory agent, allantoin, bisabolol, anti-free radical agent, vitamin E or derivative thereof, soothing agent, bluet or cornflower water, plant extract, depigmenting agent, biological active agent, urea, amino acid, vitamin or derivative thereof, protein, salicylic acid or derivative thereof, α-hydroxy acid, pyrrolidone carboxylic acid or salt thereof and/or ceramide.

* * * * *